US007311837B2

(12) United States Patent
Stein et al.

(10) Patent No.: US 7,311,837 B2
(45) Date of Patent: Dec. 25, 2007

(54) PROCESS FOR THE CONTINUOUS RECOVERY OF FREE TARTARIC ACID FROM RAW MATERIALS CONTAINING POTASSIUM HYDROGENTARTRATE

(75) Inventors: Dieter Stein, Wiesbaden (DE); Rudolf Bonsch, Mainz (DE); Klaus Erb, Goslar (DE)

(73) Assignee: Lurgi AG, Frankfurt (DE)

( * ) Notice: Subject to any disclaimer, the term of this patent is extended or adjusted under 35 U.S.C. 154(b) by 335 days.

(21) Appl. No.: 10/789,704

(22) Filed: Feb. 26, 2004

(65) Prior Publication Data

US 2004/0232078 A1 Nov. 25, 2004

(30) Foreign Application Priority Data

Feb. 26, 2003 (DE) ............... 103 08 045

(51) Int. Cl.
*B01D 11/00* (2006.01)

(52) U.S. Cl. ............ 210/638; 23/299; 23/300; 210/663; 210/669; 210/774; 210/787; 210/804; 426/495; 562/585

(58) Field of Classification Search ............. 210/259, 210/638, 663, 669, 774, 787, 804, 805, 806; 23/295 R, 299, 300; 426/271, 490, 495, 426/524; 562/580, 585; 435/144
See application file for complete search history.

(56) References Cited

U.S. PATENT DOCUMENTS

| 3,114,770 A | * | 12/1963 | Dabul .................. 562/585 |
| 3,963,700 A | * | 6/1976 | Philip .................. 536/4.1 |
| 4,560,565 A | * | 12/1985 | Wucherpfennig et al. ............ 426/330.4 |
| 4,781,809 A | * | 11/1988 | Falcone, Jr. .............. 204/537 |
| 4,889,743 A | * | 12/1989 | Tazawa et al. ............ 426/495 |
| 5,268,283 A | * | 12/1993 | Mothes et al. ............. 435/144 |
| 6,534,678 B1 | | 3/2003 | Bonsch et al. |
| 6,670,505 B1 | * | 12/2003 | Collins et al. ............. 562/580 |
| 6,790,429 B2 | * | 9/2004 | Ciampi ................. 423/594.1 |
| 2003/0185959 A1 | * | 10/2003 | Singh et al. ............ 426/590 |
| 2005/0020853 A1 | * | 1/2005 | Kuroda et al. ............. 562/580 |

FOREIGN PATENT DOCUMENTS

| AU | 749707 | 3/1999 |
| DE | C-264005 | 3/1883 |
| DE | A-19819884 | 5/1998 |
| EP | 965576 | 4/1999 |
| EP | 1454984 | 1/2004 |
| FR | A-2646421 | 4/1989 |
| RO | 88445 | 1/1986 |
| SU | 390067 | 10/1973 |

OTHER PUBLICATIONS

Derwent Translated Abstract for Soviet Union Publication SU 390,067, published Oct. 26, 1973.*

* cited by examiner

*Primary Examiner*—Joseph Drodge
(74) *Attorney, Agent, or Firm*—Kenyon & Kenyon LLP

(57) ABSTRACT

In a process for the continuous recovery of free tartaric acid from raw materials containing potassium hydrogentartrate, the same are mixed with water and the potassium hydrogentartrate is dissolved. The process is improved in that the suspension is decanted, the clarified liquid is refiltered, the filtrate is cooled to crystallization temperature under a vacuum, the potassium hydrogentartrate crystals formed are dissolved, the solution is subjected to a cation exchange, and the tartaric acid solution obtained is evaporated.

12 Claims, 1 Drawing Sheet

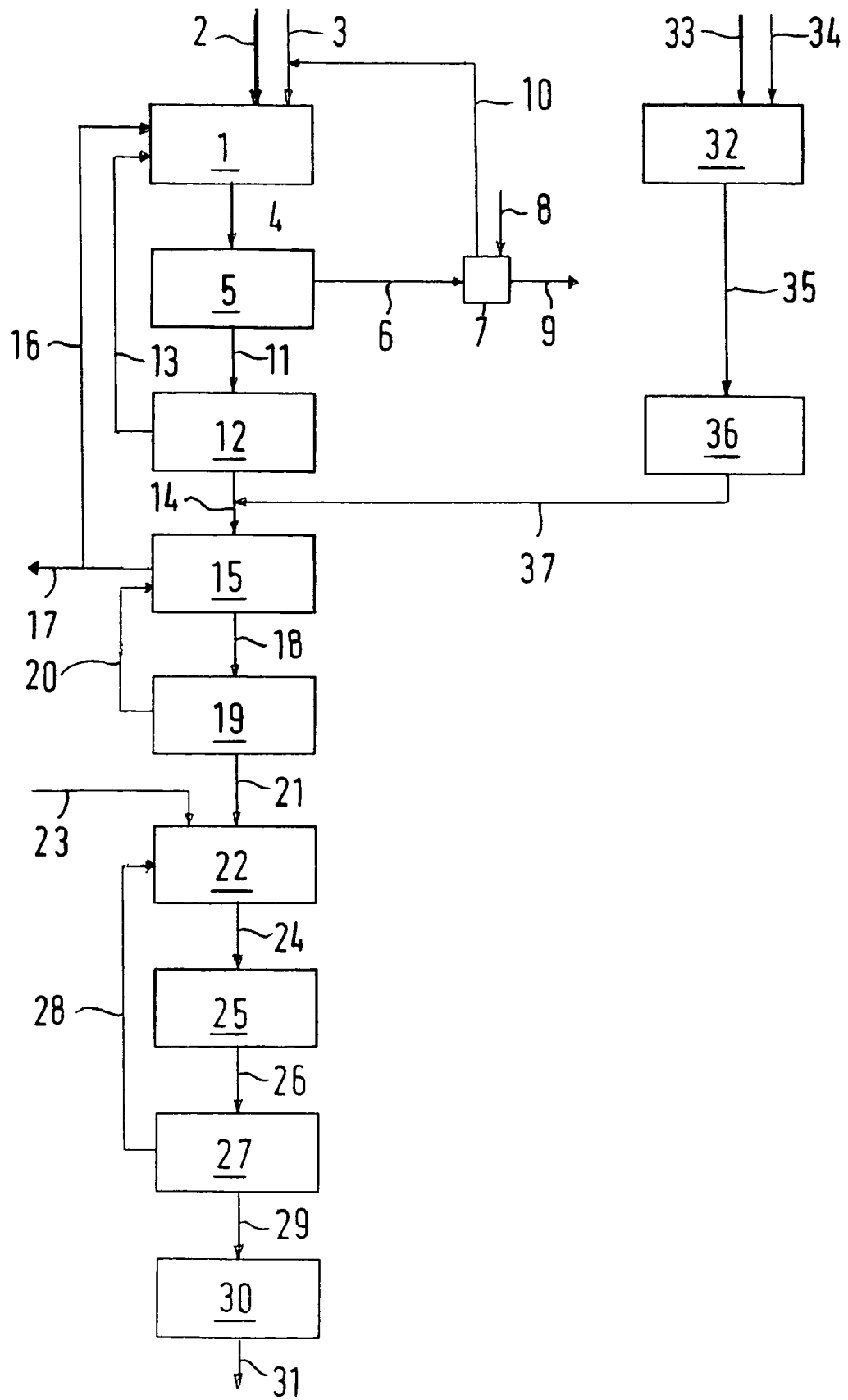

PROCESS FOR THE CONTINUOUS RECOVERY OF FREE TARTARIC ACID FROM RAW MATERIALS CONTAINING POTASSIUM HYDROGENTARTRATE

FIELD OF THE INVENTION

The present invention relates to a process for the continuous recovery of free tartaric acid ($H_6C_4O_6$) from raw materials containing at least 5.0 wt % potassium hydrogentartrate ($KH_5C_4O_6$) in dry matter, in particular from byproducts obtained during wine preparation, such as tartar, wine yeast or the like, in that the raw materials are mixed with water and the potassium hydrogentartrate is dissolved.

BACKGROUND INFORMATION

For the most part, the tartaric acid used in the industry is produced from byproducts containing potassium hydrogentartrate, which are obtained during wine preparation, such as tartar, wine yeast, marc, distillation residues, calcium tartrate, etc. In the better known processes, potassium hydrogentartrate is obtained by precipitation; the raw materials to be processed either are attacked with an acid and potassium hydrogentartrate is precipitated from the solution obtained by means of a basic agent or the raw materials are treated with a basic agent and the potassium hydrogentartrate is precipitated by adding an acid.

In the process described in DE-C-264005, the raw materials to be processed are roasted and treated with basic and acid agents such that both a solution of a neutral tartrate and a solution of a free tartaric acid are obtained. By mixing the two solutions, the tartaric acid is precipitated as potassium hydrogentartrate.

From FR-A-2646421, there is known a process for producing tartaric acid, in which the bitartrates contained in the raw materials are neutralized to obtain soluble tartrates. The aqueous solution of the tartrates is subjected to an electrodialysis, in which the ion exchange is effected on semipermeable membranes, for the purpose of producing a tartaric acid solution. The construction and operation of such an electrodialysis plant requires quite a considerable effort. In addition, the tartrate solutions subjected to the ion exchange must be free of organic substances, as the same would otherwise be decomposed during electrodialysis to form ammonia.

DE-A-19819884, is concerned with a process of producing tartaric acid from raw materials whose dry matter consists of at least 5.0 wt % potassium hydrogentartrate, in which potassium hydrogentartrate is first converted to dipotassium tartrate ($K_2H_4C_4O_6$) by stirring with aqueous potassium hydroxide solution. The aqueous solution formed is stirred at a pH-value of 2 to 5 upon removal of impurities by filtration in a precipitation stage with added acid. The added acid is preferably tartaric acid recirculated from the process. From the formed suspension containing potassium hydrogentartrate crystals, the potassium hydrogentartrate crystals are separated, washed with water, producing an aqueous solution saturated with potassium hydrogentartrate of at least 80 wt %. Potassium is removed from this solution, and from the aqueous tartaric acid solution formed, water is at least partly removed. During the conversion of potassium hydrogentartrate by means of aqueous potassium hydroxide solution to obtain dipotassium tartrate, the organic compounds contained therein, such as phenolates, sugar polymers, slimy substances and other cell ingredients, are disadvantageously dissolved, which greatly impedes filtration.

SUMMARY OF THE INVENTION

It is the object of the present invention to design the above-described process for the recovery of free tartaric acid from raw materials containing at least 5.0 wt % potassium hydrogentartrate in dry matter, in particular from byproducts obtained during wine preparation, such as tartar, wine yeast or the like, such that the filter cake obtained during the filtration of the aqueous solution from the impurities to be separated does not impede the formation of the filtrate.

The object is accomplished wherein a suspension (solid-liquid mixture) consisting of solids and potassium hydrogentartrate dissolved in water is decanted and the clarified liquid obtained thereby is supplied to a microfiltration for separating microfine solid particles. The filtrate formed thereby is cooled to crystallization temperature under a vacuum for the purpose of crystallizing the potassium hydrogentartrate. The potassium hydrogentartrate crystals formed are centrifuged for the purpose of spinning off liquid and are subsequently dissolved in water. From the aqueous potassium hydrogentartrate solution, the potassium is removed by ion exchange, and the tartaric acid solution obtained is evaporated by forming tartaric acid crystals. By separating potassium hydrogentartrate from the raw materials by means of water, the organic impurities contained in the raw materials are largely not dissolved and form a filter cake both during decanting and during the microfiltration of the clarified liquid obtained during decanting, which filter cake does not impair the separation of the filtrate. Due to the cooling crystallization of the filtrate performed under a vacuum, the addition of acid, in particular the recirculation of process tartaric acid, can be omitted. It is thus advantageously possible to design both a plant for the cation exchange and a plant for the evaporation of the tartaric acid solution 50% smaller than the corresponding plants which are required for performing the process in accordance with DE-A-19819884.

BRIEF DESCRIPTION OF THE DRAWING

The FIGURE schematically shows a basic flow diagram of an embodiment of the invention.

DETAILED DESCRIPTION

The invention is explained in detail and by way of example with reference to the basic flow diagram shown in the FIGURE.

To a heatable stirred tank (1), wine yeast, as raw material containing potassium hydrogentartrate, is charged via conduit (2) and water is charged via conduit (3) and mixed intensively. The suspension (solid-liquid mixture) formed thereby is discharged from the stirred tank (1) via conduit (4) and supplied to a decanter (5), by means of which the solids chiefly consisting of wine yeast are separated from the liquid. The solids discharged from the decanter (5) via conduit (6) are cleaned in another decanter (7) severing as a washing means, to which water is supplied via conduit (8), and are withdrawn via conduit (9) and supplied to a further use, e.g. as fodder yeast. The washing water obtained is recirculated to conduit (3) via conduit (10). The clarified liquid freely flowing out of the decanter (5) via conduit (11) is supplied to a ceramic microfilter means (12), in order to separate solid particles possibly still present in the clarified liquid, which are recirculated to the stirred tank (1) via conduit (13). The filtrate containing dissolved potassium hydrogentartrate is supplied via conduit (14) to a crystallizer

(15) consisting of one or more stages, in which potassium hydrogentartrate is crystallized by cooling the filtrate to a temperature of 5° C. under a vacuum of 0.007 bar. If necessary, there is a possibility of arranging a non-illustrated activated carbon filter between the ceramic microfilter means (12) and the crystallizer (15) for decolorizing the filtrate. The liquid formed during the cooling crystallization is partly recirculated to the stirred tank (1) via conduit (16), whereas the remaining amount is discharged from the process via conduit (17). The potassium hydrogentartrate crystals discharged from the crystallizer (15) via conduit (18) are supplied to a centrifuge (19), in which the liquid still adhering to the potassium hydrogentartrate crystals is spun off. The liquid obtained thereby is recirculated to the crystallizer (15) via conduit (20). The potassium hydrogentartrate crystals leaving the centrifuge (19) via conduit (21) are charged to a heatable stirred tank (22), in which the potassium hydrogentartrate crystals are dissolved at temperatures of 75-95° C. by adding water flowing in via conduit (23). From the stirred tank (22), the solution largely saturated with potassium hydrogentartrate is withdrawn via conduit (24), then passed over an activated carbon bed (25) for decoloration and thereafter supplied via conduit (26) to a cation exchanger (27) for removing the $K^+$ ions. A part of the solution containing 10 to 20% tartaric acid is recirculated from the cation exchanger (27) to the stirred tank (22) via conduit (28), whereas the residual part of the tartaric acid solution enters an evaporator (30) via conduit (29) and is evaporated therein by forming tartaric acid crystals. The tartaric acid crystals formed are discharged from the process via conduit (31).

An advantageous aspect of this basic flow diagram is that tartar supplied via conduit (33) and water flowing in via conduit (34) are mixed in a heatable stirred tank (32), the mixture is charged to a ceramic microfilter means (36) via conduit (35), and the filtrate formed is fed via conduit (37) into conduit (14) leading to the crystallizer (15).

Wine yeast having a content of 8.5 wt % potassium hydrogentartrate in dry matter, which is obtained during wine preparation, is intensively mixed in the stirred tank (1) with 3.0 kg water per kg wine yeast at a temperature of about 80° C. for a maximum of 60 min., in order to completely separate the potassium hydrogentartrate from the wine yeast. Subsequently, the aqueous solution having a temperature of about 80° C. is separated by means of a decanter (5) into a sediment consisting of solid organic particles of 30 wt % in dry matter and a clarified liquid containing 2.8 wt % potassium hydrogentartrate. After the passage of this liquid through a ceramic filter (12), potassium hydrogentartrate is crystallized out of this filtrate in a crystallizer (15) at a temperature of about 5° C. and a vacuum of 0.007 bar. The potassium hydrogentartrate crystals largely liberated from the liquid by means of a centrifuge (19) are dissolved in a stirred tank (22) by adding water, and the solution is charged to a cation exchanger (27) in which 15% tartaric acid is produced, which is subsequently evaporated in an evaporator (30) by forming tartaric acid crystals.

The invention claimed is:

1. A process for the continuous recovery of free tartaric acid from raw materials containing at least 5.0 wt % potassium hydrogentartrate in dry matter comprising mixing the raw materials with water and dissolving potassium hydrogentartrate to form a suspension of potassium hydrogentartrate, decanting the suspension to obtain a clarified liquid, subjecting the clarified liquid to a microfiltration to form a microfiltration filtrate, vacuum cooling the microfiltration filtrate to crystallization temperature to form potassium hydrogentartrate crystals, centrifuging the potassium hydrogentartrate crystals, dissolving the potassium hydrogentartrate crystals in water, removing the potassium from the aqueous potassium hydrogentartrate solution by ion exchange, and forming tartaric acid crystals by evaporating the tartaric acid solution.

2. The process of claim 1, wherein the raw material is wine yeast, tartar, or a byproduct material obtained during wine preparation.

3. The process of claim 1, wherein the filtrate obtained by a microfiltration of aqueous tartar solution is added to the filtrate provided for the cooling crystallization.

4. The process as claimed in any of the claims 1 to 3, wherein the liquid obtained during decanting is at least partly recirculated to the process.

5. The process as claimed in any of the claims 1 to 3, wherein the liquid obtained during the microfiltration is at least partly recirculated to the process.

6. The process as claimed in any of the claims 1 to 3, wherein the liquid obtained during the cooling crystallization is at least partly recirculated to the process.

7. The process as claimed in any of the claims 1 to 3, wherein the liquids obtained during decanting, microfiltration, and cooling crystallization are at least partly recirculated to the process.

8. The process as claimed in any of the claims 1 to 3, wherein the liquid obtained during decanting is at least partly recirculated to the process and wherein the liquid is recirculated to the suspension containing solids and potassium hydrogentartrate dissolved in water.

9. The process as claimed in any of the claims 1 to 3, wherein the liquid obtained during the microfiltration is at least partly recirculated to the process and wherein the liquid is recirculated to the suspension containing solids and potassium hydrogentartrate dissolved in water.

10. The process as claimed in any of the claims 1 to 3, wherein the liquid obtained during the cooling crystallization is at least partly recirculated to the process and wherein the liquid is recirculated to the suspension containing solids and potassium hydrogentartrate dissolved in water.

11. The process as claimed in any of the claims 1 to 3, wherein the liquids obtained during decanting, microfiltration, and cooling crystallization are at least partly recirculated to the process and wherein the liquid is recirculated to the suspension containing solids and potassium hydrogentartrate dissolved in water.

12. The process as claimed in any of claims 1 to 3, wherein the cooling crystallization is performed at a temperature of 5 to 15° C. and under a vacuum of 0.007 to 0.015 bar.

* * * * *